United States Patent [19]
Saadat et al.

[11] Patent Number: 5,928,249
[45] Date of Patent: Jul. 27, 1999

[54] CERVICAL DAM

[75] Inventors: Vahid Saadat, Redwood Shores; Seth A. Stabinsky, Palo Alto, both of Calif.

[73] Assignee: Gynecare, Inc., Menlo Park, Calif.

[21] Appl. No.: 08/891,592

[22] Filed: Jul. 11, 1997

[51] Int. Cl.⁶ ........................................... A61B 17/42
[52] U.S. Cl. ................................. 606/119; 604/19
[58] Field of Search .......................... 606/119–126, 1, 606/135, 193; 604/19, 22, 27, 28, 30, 35, 41, 43, 54, 55; 128/830–841; 600/573, 574, 591

[56] References Cited

U.S. PATENT DOCUMENTS

| | | |
|---|---|---|
| 3,404,682 | 10/1968 | Waldron . |
| 4,369,219 | 1/1983 | Goepp et al. . |
| 4,430,076 | 2/1984 | Harris ........................ 606/119 |
| 4,543,949 | 10/1985 | Goepp et al. . |
| 4,606,336 | 8/1986 | Zeluff . |
| 4,932,422 | 6/1990 | Ragheb . |
| 5,357,980 | 10/1994 | Seitzinger ................ 606/119 |
| 5,385,553 | 1/1995 | Hart et al. . |
| 5,411,483 | 5/1995 | Loomas et al. . |
| 5,536,243 | 7/1996 | Jeyendran . |

FOREIGN PATENT DOCUMENTS

| | | | |
|---|---|---|---|
| 0319394 | 6/1989 | European Pat. Off. ........ 606/119 |

OTHER PUBLICATIONS

V. Rimkus and K. Semm, Hysteroscopic Sterilization—a Routine Method? 22 Int. J. Fertil: 121–124 (1977).

Erich E. Brueschke, M.D. et al., A Steerable Hysteroscope and Mechanical Tubual Occlusive Devices, in Advcances In Female Sterlization Techniques, 182–98 (John J. Sciarra, M.D., Ph.D. et al. eds. 1976.

WISAP Product Catalog, Pertubation–Zubehor, "Pertubation–Accessories" (8 pages).

*Primary Examiner*—Glenn K. Dawson

[57] ABSTRACT

Cervical dam for capturing liquid draining from uterus during gynecological procedures while simultaneously providing an aperture through the cervical dam for insertion and manipulation of a medical device. The aperture may be a preformed slit elastomeric aperture, a duck billed valve, a multi-disc elastomeric valve, or a universal seal. The cervical dam includes a drainage port through the body of the cervical dam, a drainage tube attached to the drainage port, and a handle, which may be detachable, affixed to the cervical dam for placement, manipulation and removal of the cervical dam. Also disclosed are methods for performing a gynecological procedure by placing a cervical dam over the cervical canal inserting a medical instrument through the cervical dam into the cervical canal, performing a procedure, and withdrawing the medical instrument, and by determining the amount of fluid input to a patient during the procedure and the amount drained from the patient during and after the procedure, and comparing the two.

9 Claims, 8 Drawing Sheets

CERVICAL DAM

BACKGROUND OF THE INVENTION

The invention relates to a device and method for controlling and monitoring liquid draining from the uterus during medical procedures within the uterus, and more particularly to a device and method permitting the introduction of liquid into the uterus and controlling and monitoring drainage from the uterus while simultaneously permitting the entry into and manipulation within the uterus of a medical instrument or device.

In their practice, gynecologists often find it useful to introduce liquid into the uterus as an aspect of treatment or of a diagnostic procedure. Currently, a gynecological procedure may be performed in a surgical suite at a hospital where the patient may be draped to catch any such liquid if it drains from the uterus and direct the flow of the liquid to a container. The surgical suite is also generally designed and staffed to deal with spillage and facilitate clean-up. The procedure may be performed in an office setting, however, which generally lacks the staff and facilities of the surgical suite for dealing with any such spillage.

As liquid in the uterus drains out through the cervix into the vagina and then out of the body, several problems may be created. One problem that may result is the mess and hazard of spillage. The liquid may spill out into the area where a gynecologist is working, creating an inconvenient situation. Such spillage is particularly a problem where the procedure involves the use of small diameter instruments inserted through the cervix, the use of low viscosity liquid in the uterus, the dilation of the cervix, and where the procedure is performed in an office setting rather than in a surgical suite.

Contact between various tissue and the liquid draining from the uterus may also be a problem. The liquid used may have certain properties such as high temperature so that the physician would prefer not to expose vaginal tissue, or the skin of the patient or physician to contact with the liquid. Therefore it would be advantageous to devise an apparatus and method to control the drainage of such liquid to prevent exposing the patient's vaginal tissue or the skin of the patient or doctor to such liquid.

A third potential problem created by uncontrolled drainage is the inability to monitor the amount of fluid absorbed by the patient during the procedure. The interior of the uterus is highly vascularized, and the uterus is open to the peritoneal cavity through the fallopian tubes. As a result, liquid introduced into the uterus is sometimes absorbed by the patient's bloodstream or may migrate through the fallopian tubes into the peritoneal cavity. It is important to monitor the amount of liquid input and the amount drained to estimate the amount of such liquid absorbed into the patient's system so that a physician can take appropriate action if the amount absorbed by the patient indicates that action is necessary. Such action by a physician might include, for example, stopping the procedure, administering drugs such as diuretics, or both.

If the liquid drains out of the patient onto the floor or soaks into surgical drapes, it becomes difficult to determine how much of the liquid input during a procedure drained out and how much was absorbed by the patient. A method of accurately monitoring the outflow of liquid from the uterus would be advantageous both when the procedure is performed in an office setting and when the procedure is performed in a surgical suite.

One important and common procedure used by gynecologists to visualize the interior of the uterus is hysteroscopy. A hysteroscope is a specialized endoscope which, in hysteroscopy, is introduced into the patient through the vagina and the cervix to view the interior surface of the uterus. The hysteroscope may be either a contact hysteroscope that provides viewing of the tissue against which the tip of the hysteroscope is placed, or may be a panoramic hysteroscope which may view the tissue at some distance from the tip of the hysteroscope and, as the name implies, provide a more panoramic view.

The inside of the uterus generally has its walls closely opposed so that distension of the uterus is necessary to create sufficient separation between the walls for viewing by a hysteroscope, particularly the panoramic hysteroscope. Therefore hysteroscopy usually begins with distending the interior cavity of the uterus by introduction of distension media into the uterus under pressure to separate the uterine walls and create space for viewing the endometrial tissue of those walls. Once the uterus is thus distended, it is generally maintained in the distended condition by maintaining the distension media within the uterus under slight pressure.

Hysteroscopes may be diagnostic or operative. Diagnostic hysteroscopes are used primarily to view and evaluate the condition of the tissue within the uterus. Operative hysteroscopes are generally carried within a stainless steel tube called a surgical sheath. The surgical sheath may contain various surgical tools such as semi-rigid sensors, clamps, or surgical electrodes that may be manipulated from outside the body to perform procedures such as biopsy of tissue, resectoscopic surgery, laser surgery and electrosurgery in a liquid environment.

The hysteroscope, whether diagnostic or operative, is generally tubular in shape and is inserted through the cervix into the uterus. The portion of a typical hysteroscope positioned within the uterus terminates in a lens and is provided with cold light generally from a light source located outside the body which is filtered and transmitted into the uterus by fiber optics. The portion of the hysteroscope which extends out of the patient's body may terminate in an eyepiece for viewing through the lens or may be fitted to a video camera so that the image from the lens may be displayed on a video screen and simultaneously recorded. Both types of hysteroscopes are generally contained within a stainless steel sheath that has channels, for example, for the inflow of a distension media and for the aspiration of fluid. If the hysteroscope is an operative hysteroscope, the surgical sheath will generally have additional channels for various surgical instruments. Because of the additional channels, operative hysteroscopes are generally but not always thicker in diameter than diagnostic hysteroscopes.

The typical diagnostic hysteroscope is usually tubular in shape and has an outer diameter of 3 to 5 millimeters. The typical operative hysteroscope may be 9 millimeters in diameter. Improvements in surgical instruments have provided surgical electrodes as small as 1.7 millimeters and allow operative hysteroscopes as small as 5 millimeters to be used for electrosurgical procedures. The smaller diameter is generally preferable because it is less traumatic to the patient. However, electrosurgical procedures are generally performed in a liquid environment, in which case the introduction of a significant amount of liquid may be involved. Any leakage problem could be exacerbated if a smaller diameter instrument is used.

The uterus is open through the cervix into the vagina, the vagina is open out of the patient, and distension fluid initially introduced into the uterus will drain out of the patient if not contained. Even if the distension media initially introduced into the uterus does not significantly drain out, it is often necessary to introduce additional distension media into the uterus during a hysteroscopic procedure. Particularly with a hysteroscope having a small diameter or with distension medium having low viscosity, the fit between the hysteroscope and the cervix may be loose enough to allow the distension medium to drain out during hysteroscopy. This problem is exacerbated if the cervix is dilated for any reason.

Various methods for forming a tighter fit between the cervix and an inserted hysteroscope have been suggested, including the use of specialized tenacula to compress the cervix around the inserted hysteroscope, or the use of a purse string suture to tighten the cervix around the inserted hysteroscope. These methods involve additional time and manipulation and may increase the trauma to the tissue manipulated in this way. A simple, fast and less traumatic method of controlling the drainage of distension media would be advantageous.

Hysteroscopy may be performed in a hospital setting such as a surgical suite, or if appropriate, in a doctor's office. It is often preferable to perform such procedures in the office setting because hysteroscopy performed in an office is generally more convenient, less expensive and less time consuming, and may be accomplished using fewer personnel than when it is performed in a hospital. However, uncontrolled drainage of distension media may make such procedures difficult to perform in the office setting. In both office and hospital settings, the inability to accurately monitor the amount of fluid absorbed by the patient, and undesirable contact between vaginal tissue or skin and liquid used in the procedure are problems.

Some hysteroscopes have a viewing direction in line with the surgical sheath generally referred to as 0 degrees, and some have a viewing line angled outward at 30 degrees from the line of the surgical sheath. Anatomical features of the uterus that gynecologists commonly need to view by hysteroscopy are the tubal ostia which are at the entrance of the fallopian tubes into the uterus. In cross-section, the uterus is generally shaped as an inverted triangle, with the cervix at the lower point open to the vagina through the external os, and the fundus of the uterus, the area between the two tubal ostia, being the top line of the inverted triangle. In order to view the tubal ostia, a hysteroscope with a 0 degree line of sight inserted through the cervix may have to be angled significantly toward each upper corner of the uterus. If the hysteroscope is inserted directly into the cervix, such manipulations may result in twisting and other movement of the hysteroscope directly against the tissues of the cervix, the cervical canal and, in extreme cases, the uterus. A device whereby an instrument inserted into the cervix and moved and manipulated, for example angled for a view toward the tubal ostia, without putting direct pressure against the internal tissue of the cervix would be advantageous.

The present invention provides a convenient device and method to address and ameliorate the above described problems.

SUMMARY OF THE INVENTION

The present invention is directed to a cervical dam and method whereby the drainage of material discharged from the uterus during a gynecological procedure is collected by a dam positioned over the external os at the entrance to the cervical canal while simultaneously allowing the introduction and manipulation of an instrument such as a hysteroscope. A device having the features of the present invention comprises a cervical dam having a body with a generally circular base with the base sized and configured to snugly surround a human cervix, and having an aperture located in the body. When the base is positioned around the cervix, a membrane forming the body of the dam forms a barrier beneath the cervical canal, and the aperture is positioned centrally, directly beneath the external os. A space exists between the external os and the membrane, forming a cavity. An instrument such as a hysteroscope to be slidably introduced through the cervical canal and into the uterus. While the instrument is in place through the aperture, a relatively fluid-tight seal is maintained between the aperture and the instrument. In this way, any liquid draining from the uterus during the procedure will not drain out in an uncontrolled manner but rather be collected in the cavity formed between the cervical dam and the external os.

The generally circular base may be elastomeric in order to snugly grasp the exterior of the cervix and retain the cervical dam in place. An inflatable ring may be contained within the base to adjust the force attaching the base to the cervix. An inflatable bladder may be placed around the upper portion of the cervical dam within the membrane, and may have ridges on a roughened surface to aid in gripping the cervix.

The cervical dam may have a drainage port located therethrough, and liquid captured behind the cervical dam may be evacuated through the drainage port. A drainage tube may be attached to the drainage port and fluid drained through the drainage port will be carried through evacuation tube. A mild vacuum may be applied to the drainage port to facilitate the evacuation of fluid. The fluid evacuated may be measured to assist in monitoring the volume of liquid used in the procedure, and fluid and tissue captured by the cervical dam may be conveniently collected for examination.

The aperture may be in the form of a pre-formed slit in the elastomeric membrane. Alternatively, a valve may be disposed within the aperture, to form a relatively fluid-tight seal with an instrument slidably inserted therethrough so that liquid within the uterus does not drain out through the cervical canal while the instrument is positioned through the valve including when the instrument is advanced or withdrawn. The valve is configured to close when there is no instrument therethrough and form a relatively fluid-tight seal when closed. The valve may be, for example, an elastomeric aperture, a duck bill valve, or a universal seal.

A handle may be located on the cervical dam of sufficient length to extend out of the patient's vagina to allow the cervical dam to be placed over the cervix at the outset of the procedure, manipulated during the procedure, and removed after the procedure, all from outside the patient. The handle may be detachable from the cervical dam, and may also be reattachable. This will allow removal of the handle during the medical procedure for the convenience of the gynecologist, and replacement of the handle at the conclusion of the procedure to facilitate convenient removal of the cervical dam.

Other features and advantages of the invention will become apparent from the following detailed description, taken in conjunction with the accompanying drawings, which illustrate, by way of example, the features of the invention.

DETAILED DESCRIPTION OF THE PREFERRED EMBODIMENTS

Figure 1:
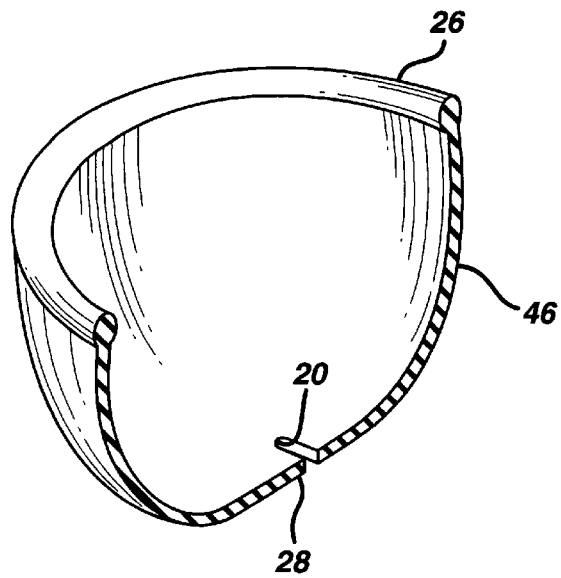
FIG. 1 is a side cut-away view of the cervical dam of the present invention.
Figure 2:
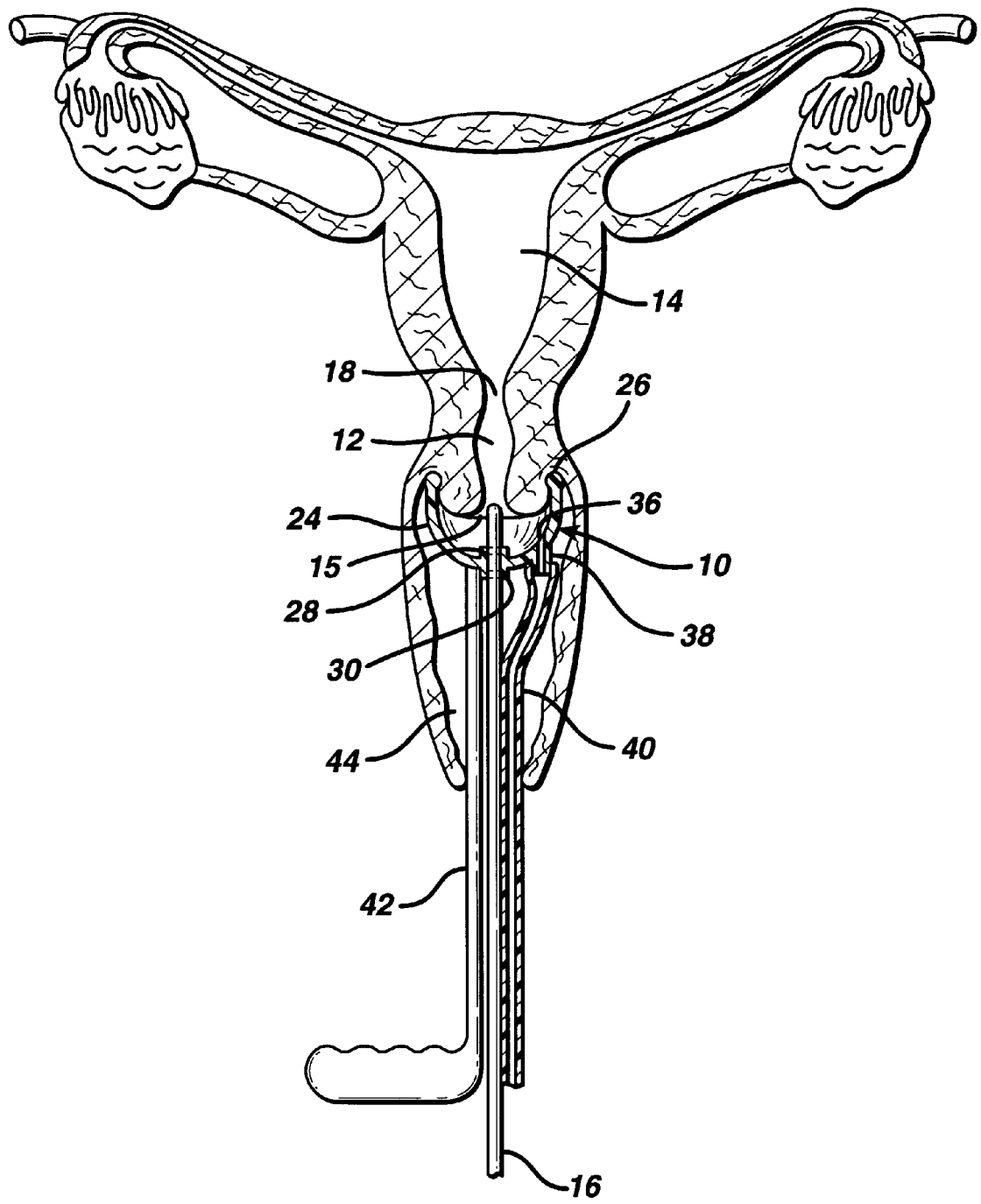
FIG. 2 is a cut-away view of an embodiment of the present invention positioned over a human cervix.

As shown in the drawings for illustrative purposes, and referring specifically to FIG. 1 and FIG. 2, the invention is embodied in a cervical dam 10 for placement over the external os of a human cervix, damming cervical canal 12 to capture liquid draining from the uterus 14 during a gynecological procedure such as a hysteroscopy. The cervical dam has a centrally located aperture 30 which allows an instrument such as a hysteroscope 16 to be inserted through the aperture into the cervical canal while the cervical dam is in place, and a relatively fluid tight seal will be formed around the instrument.

Figure 4:
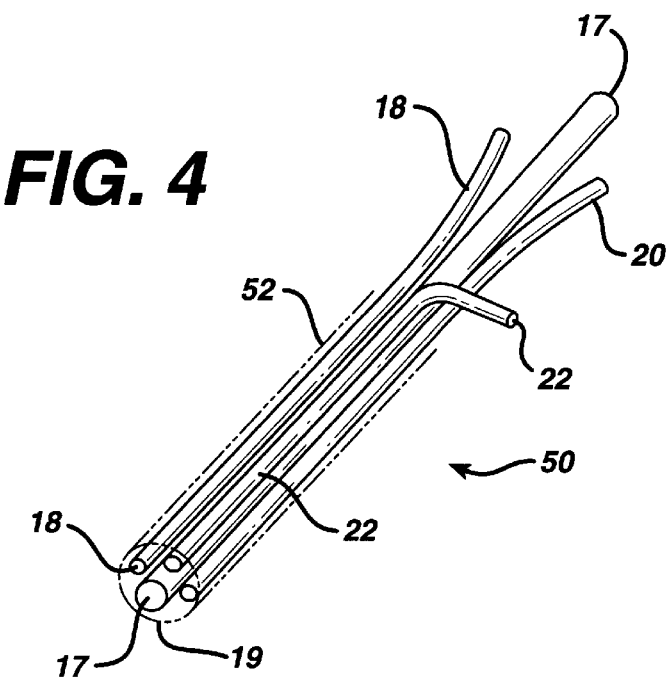
FIG. 4 is a perspective view of a medical instrument with the surgical sheath shown partially in phantom (prior art)

In hysteroscopy, an instrument known as a hysteroscope 16 is inserted into the uterus 14. The hysteroscope is a specialized endoscope used to visualize the interior of the uterus. Referring to FIG. 4 for illustrative purposes, the hysteroscope consists of a telescope 17 and a light source. The hysteroscope may be contained within a stainless steel tube sometimes called a surgical sheath which may also encase a number of tubes or channels 18, 19, 22 used to introduce surgical devices such as scissors or electrodes into the uterus, and used for the introduction of fluid into or the suction of fluid from the uterus while the surgical sheath is in place through the cervix.

In performing hysteroscopy, the gynecologist generally inserts the hysteroscope through the external os 15 into the cervix and gently dilates the uterus with fluid under low pressure to expand the uterine cavity for optimal viewing. This fluid, sometimes referred to as distension medium, may be introduced into the uterus through one of the channels in the sheath after insertion of the hysteroscope. In addition to enhancing the ability to visualize the interior of the uterus, liquid distension medium may create an appropriate liquid environment for electrosurgical procedures. Likewise, additional fluid may be introduced during hysteroscopy to maintain dilation or to purge the area at the tip of the medical instrument to clear blood or debris and enhance visibility.

The distension medium used during such procedures will vary. The uterus may be insufflated with a gas medium, usually carbon dioxide, or dilated with liquid medium. The preferred liquid media include normal saline, lactated Ringer's solution, dextrose 5% in water or water solutions, glycine, sorbitol, mannitol, and a high viscosity solution of dextran 70 in 10% dextrose. Some of the factors considered in choosing one type of distension medium over another include the optical characteristics of the fluid, such as refractive index, the isotonicity or density of the fluid which will affect its absorption into the patient's system during the procedure, viscosity, which would influence leakage during the procedure, the electrolytic nature of the substance if electrosurgery is anticipated, and the cost.

Figure 3:
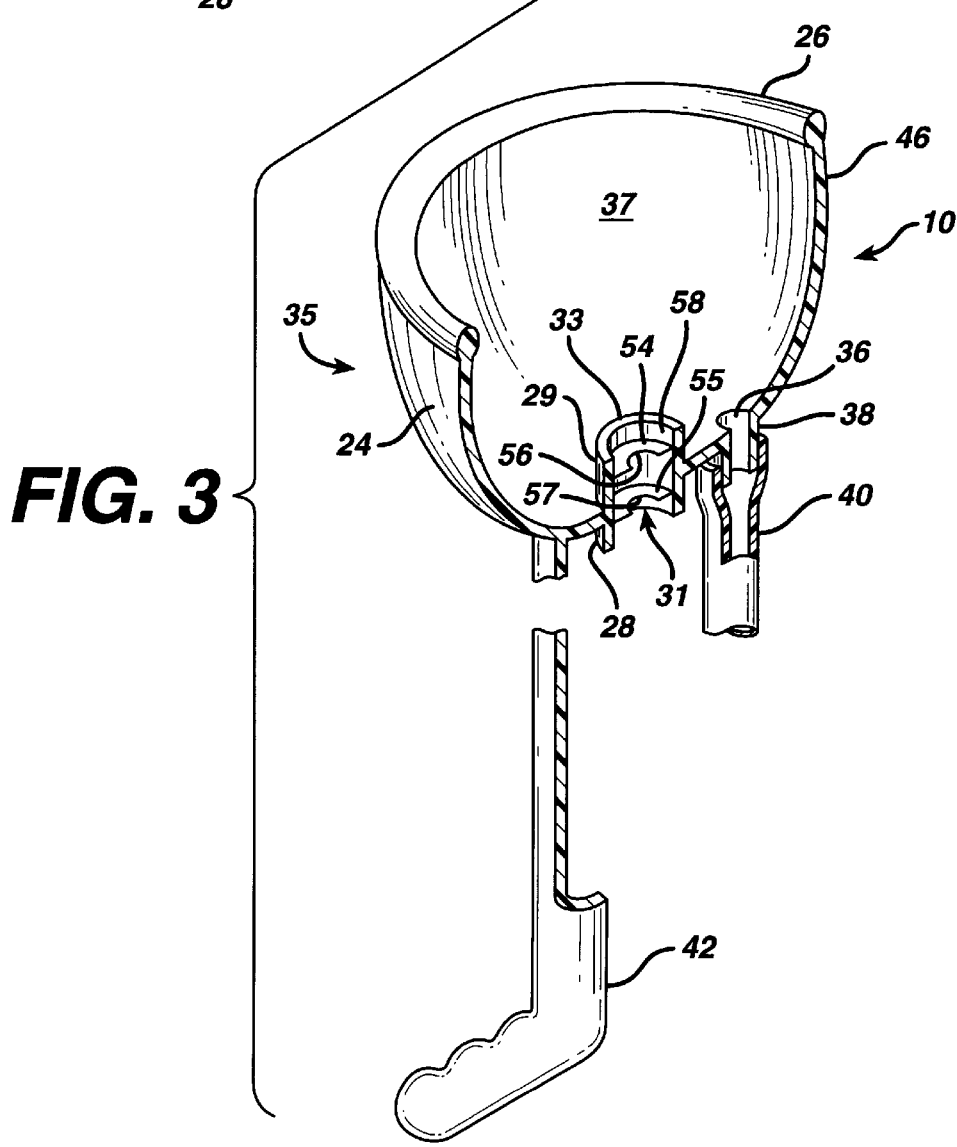
FIG. 3 is a partial cut-away perspective view of an embodiment of the present invention.

Referring to FIG. 3 for example, the cervical dam 10 may be comprised of a membrane 46 which may be a non-elastic material such as polyethylene or urethane, or other biocompatible material, or may be an elastomeric material such as latex or some other biocompatible elastomeric material. The membrane forms a generally dome-shaped body 24 having a generally convex exterior surface 35, a generally concave interior surface 37, and a generally circular base 26. The membrane will be of an appropriate material compatible with the fluid anticipated to be used as the distension medium. The membrane may be solid or may be semi-permeable as illustrated, for example, in FIG. 5, having holes therein 48 which will not permit liquid distension medium to flow through, but may allow air to flow through.

The base may be sized to snugly surround the human cervix 11 and hold the membrane across the cervical canal 12, or as an alternative method of anchoring the cervical dam, the base may be sized and configured to contact the vaginal walls and be retained between the pubic symphysis and coccyx while holding the membrane generally across the cervix (configuration not illustrated).

Figure 8:
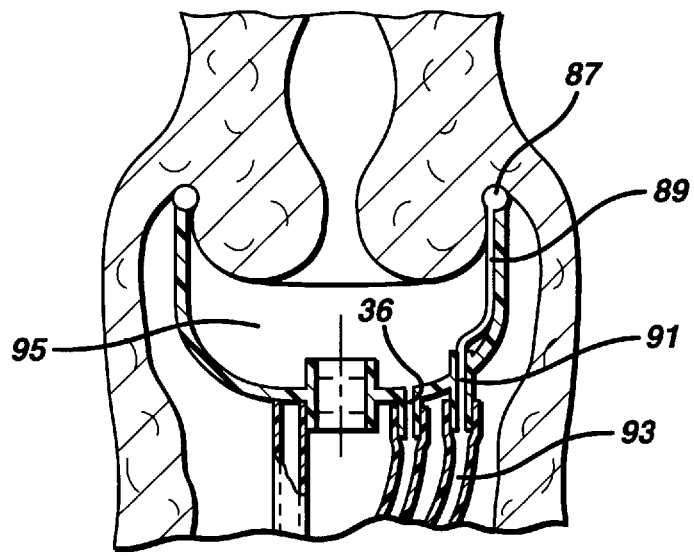
FIG. 8 is a side cut-away view of an embodiment of the present invention in place across a human cervix.
Figure 9:
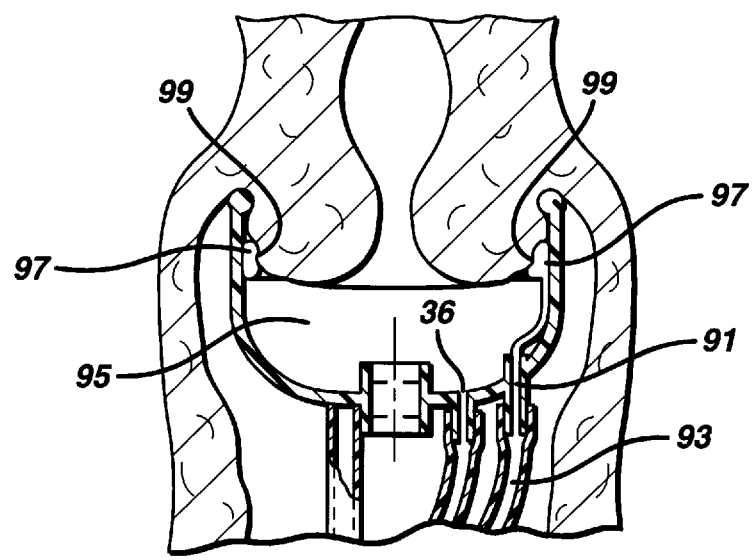
FIG. 9 is a side cut-away view of an embodiment of the present invention in place across a human cervix.

Referring to FIG. 8, there may be an inflatable ring 87 incorporated into the base, which ring is in fluid communication with an inflation port 91 through the inflation channel 89. The inflation channel is in fluid isolation from the interior cavity 95 formed between the membrane of the cervical dam and the external os of the cervix. Inflation fluid, such as an inflation gas or inflation liquid, can be placed into an inflation tube 93 and pressurized to inflate the ring 87 without introducing pressurized fluid into the interior cavity 95. Alternatively, an inflatable cuff 97, which may have a roughened exterior surface 99, may be incorporated into the cervical dam as illustrated in FIG. 9.

Referring again to FIG. 2, the dome-shaped body forms an apex 28 where it forms an aperture 30. The aperture is configured so that when a hysteroscope or other medical instrument is inserted therethrough, a relatively liquid-tight seal is formed between the instrument and the cervical dam. This aperture may be, for example, in the nature of a preformed slit 20 in a latex membrane as illustrated, for example, in FIG. 1, or contain a valve such as an elastomeric disc valve 31 as illustrated, for example, in FIG. 3, a duck bill valve 32 as illustrated, for example, in FIG. 5, or a universal seal 34 as illustrated, for example, in FIG. 6.

As illustrated in FIG. 1, an aperture may be formed as a slit 20 at the apex of an elastomeric membrane 46, for example, latex. The slit generally forms a liquid-tight closure unless a medical instrument (not shown) is forced through the preformed slit. When an instrument is forced through the slit, the edges of the slit are forced apart yet are elastomerically biased against the side of the instrument to form a generally fluid-tight seal between the membrane of the cervical dam and medical instrument. When the instrument is withdrawn, the preformed slit shuts elastomerically sufficient to again form a relatively liquid-tight closure.

As illustrated in FIG. 3, an elastomeric disc valve 31 may be formed, for example, by a generally cylindrical tube 33 having several elastomeric discs 54, 55, positioned therein, the discs having holes 56, 57, in the center of the discs. These discs are spaced apart along the cylindrical tube perpendicular with the axis of the tube, such that the holes in the center of the discs roughly align with each other along the axis of the tube. The plurality of discs aid in sealing.

Figure 5:
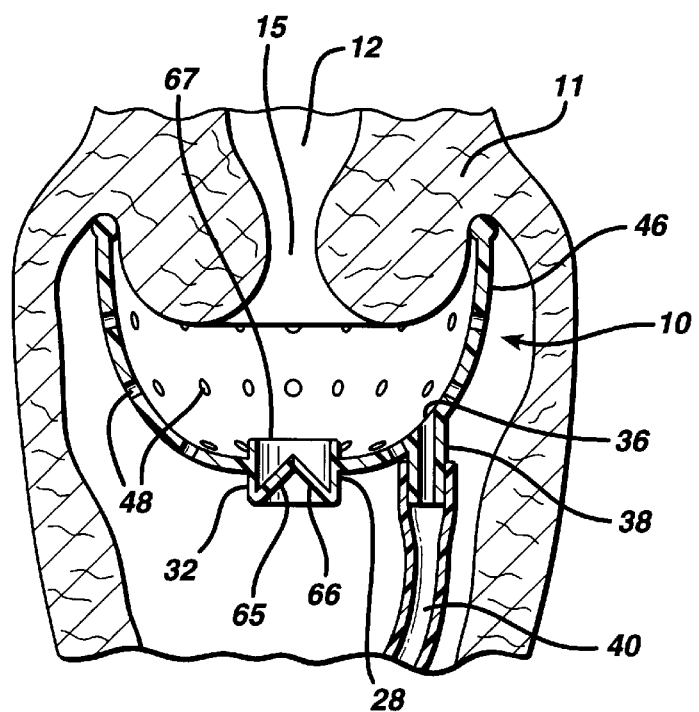
FIG. 5 is a side cut-away view of an embodiment of the present invention in place across a human cervix.
Figure 6:
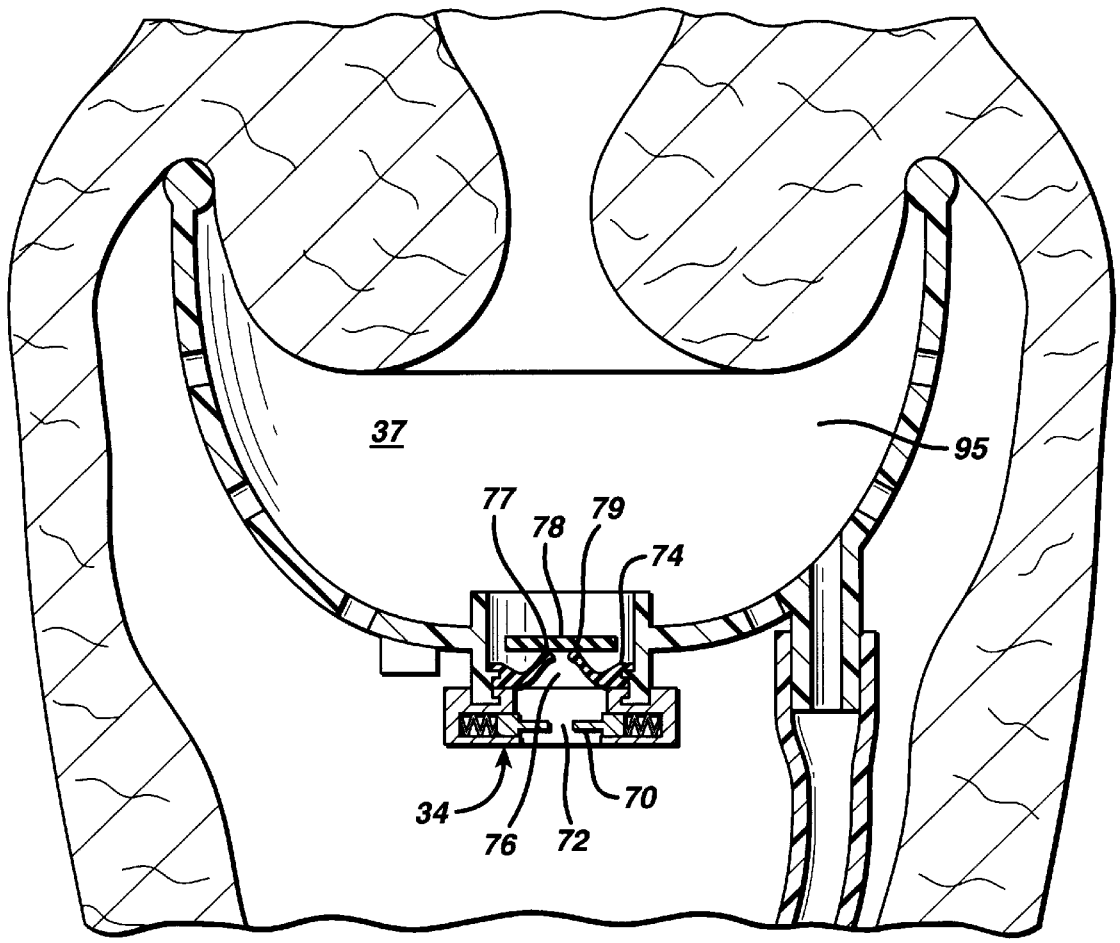
FIG. 6 is a side cut-away view of an embodiment of the present invention in place across a human cervix.

A duck bill valve 32, such as that illustrated in FIG. 5, may take the form of two elastomeric leaves 65, 66 positioned within a cylindrical tube 67 and in the closed condition, are biased against each other. The leaves are angled toward the interior of the body so that an instrument inserted into the exterior end of the cylindrical tube 67 and pushed toward the interior end forces the leaves apart as the instrument is advanced. When the instrument is inserted, the valve is in the open condition with the leaves biased against the outside surface of the instrument to form a liquid-tight seal.

Universal seals of the type for slidably introducing medical instruments or devices therethrough while maintaining a fluid-tight seal are known in the art and are described, for example, in U.S. Pat. No. 5,385,558 to Hart et al. and U.S. Pat. No. 5,411,483 to Loomas et al., incorporated herein by reference. A universal seal located in the aperture allows the introduction of tubular instruments of various diameter, while maintaining a fluid-tight seal. As shown, for example, in FIG. 6, a universal seal may comprise, for example, a laterally compliant, inwardly biased outer instrument seal 70 having an instrument port 72, an inner seal 74 which may be a rubber-like material, having an inner port 76 covered by an downwardly biased flap 78. In its closed condition, the universal seal forms a relatively liquid-tight seal. When an instrument is inserted through the instrument port 72 and through the inner port 76, the flap 78 is pushed open, forcing the universal seal into an open condition and allowing the instrument to be slidably advanced. Once the instrument is inserted into the universal seal, the edges of the instrument port 72 and the inner seal are biased against the outside surface of the instrument to form a relatively fluid-tight seal. When the instrument is withdrawn, the flap rotates against the lips 77, 79 of the inner seal 74 and creates a fluid-tight seal over the inner port 76.

The cervical dam in each of these embodiments has a cavity 95 formed between the interior surface of the membrane 37 and the external os of the cervix. Any liquid draining from the cervical canal, whether leaking around the outside of an instrument inserted into the cervix or draining without an instrument in place through the aperture, will be collected behind the membrane in the cavity and may be drained in a controlled manner, as for example, through a drainage port 36 described below.

The cervical dam in any of these embodiments may also have a drainage port 36, as illustrated, for example, in FIG. 3, for removal of fluid which may collect behind the dam when it is in place. The drainage port may in turn be provided with a tubular extension 38 onto which a drainage tube 40 may be attached. The drainage tube is in fluid communication with the interior of the cervical dam and fluid draining from the uterus collects behind the cervical dam and is drained away through the drainage port and into the drainage tube. Fluid draining through the drainage tube may be collected, as illustrated at 85 in FIG. 7B, for examination, for example for diagnostic purposes, and the amount of fluid drained may be measured (not illustrated), for example for purposes of monitoring the amount of fluid that may be absorbed by the patient during a procedure.

In some embodiments of the invention, for example FIG. 3, the wall 29 of the central tube 33 may extend inward above the internal surface 37 of the dam so that a small amount of fluid on the internal surface would not enter the internal opening 58 of the central tube, and if the drainage port 36 opens onto the internal surface at a level lower than the internal opening of the central tube, the liquid may be drained before it rises to a level sufficient to enter the internal opening.

Drainage from behind the cervical dam through the drainage tube may be enhanced by applying vacuum to the drainage tube, or drainage may be prevented by applying pressure. If the membrane is gas permeable, for example if it contains holes 48 as illustrated in FIG. 5, the vacuum may be applied without collapsing the cervical dam against the cervix if the membrane allows sufficient air to pass through it to relieve the vacuum sufficient to prevent harmful collapse of the dam. Such a semi-gas permeable membrane with holes may, if a gentle vacuum is applied, also serve to capture and evacuate fluid from the vagina in the area around the exterior of the cervical dam.

To aid in the placement of the cervical dam over the cervical canal, manipulation of the cervical dam during a gynecological procedure, and removal of the cervical dam after the procedure, the cervical dam may be provided with a handle 42, as shown in FIG. 2. Preferably the handle is of sufficient length to extend outside the vagina 44 when the cervical dam is in place over the cervical canal. The handle may be located sufficiently to one side of the body of the cervical dam to be out of the way of when the hysteroscope is inserted into the aperture. If the cervical dam is elastomeric, and particularly if it is made of thin material, generally the closer the handle fastens to the base the more pressure that can be applied to seat the dam without deforming or buckling the body. The handle may be separately attached, or may be formed as in integral part of the cervical dam.

Figure 7A:
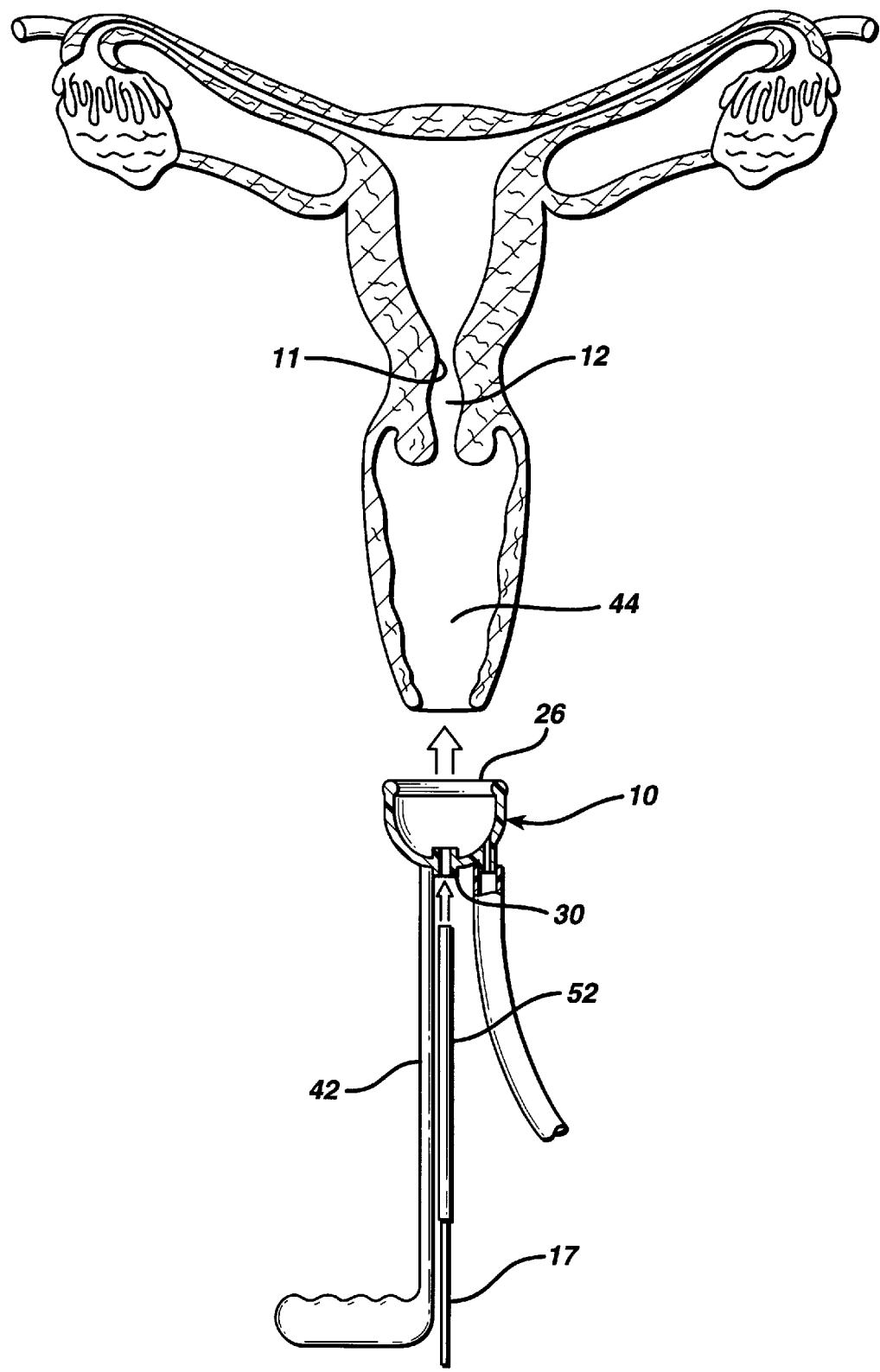
FIGS. 7A–7C are a depiction of the steps of the method of using the device of this invention in a medical procedure.
Figure 7B:
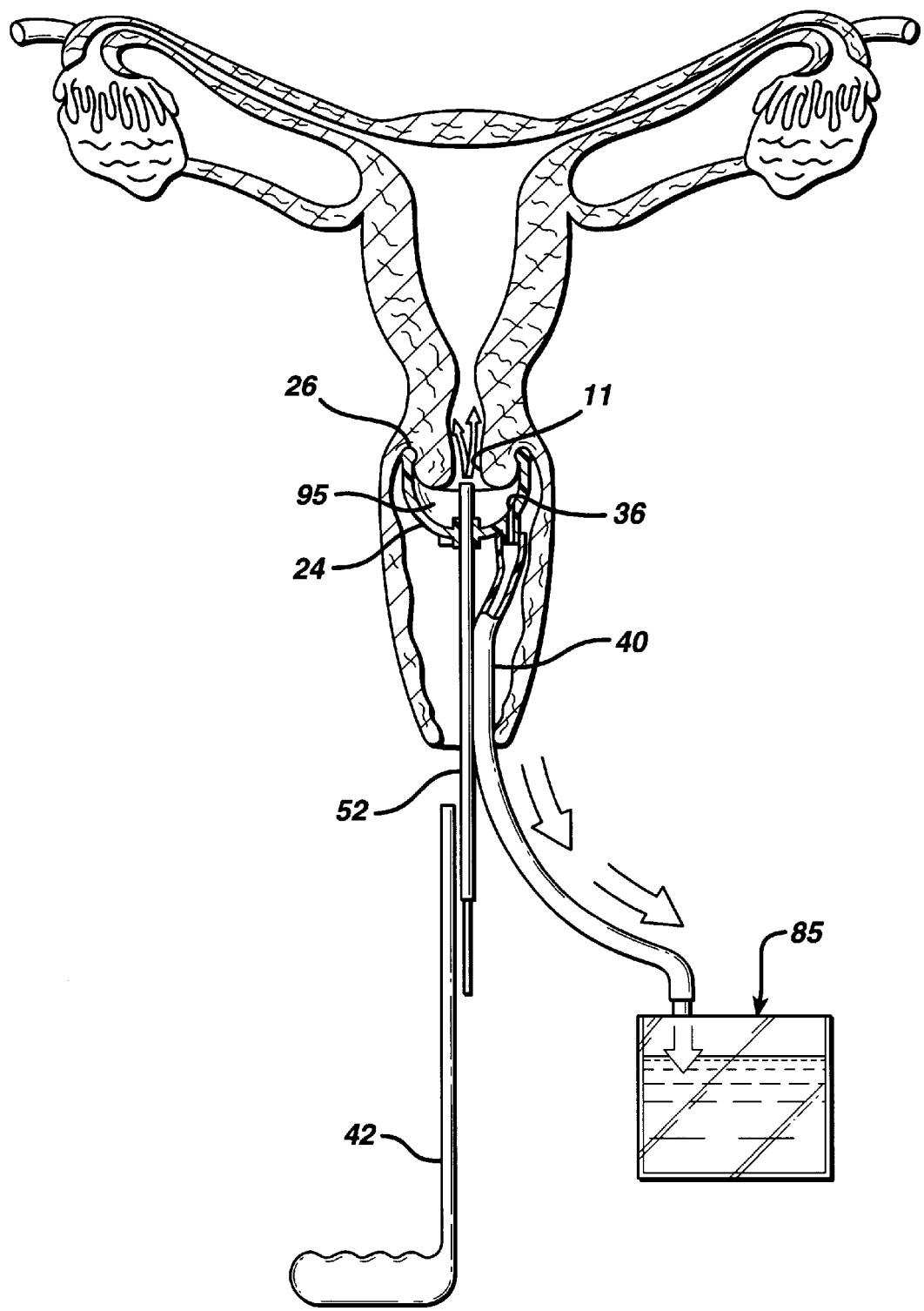
Figure 7C:
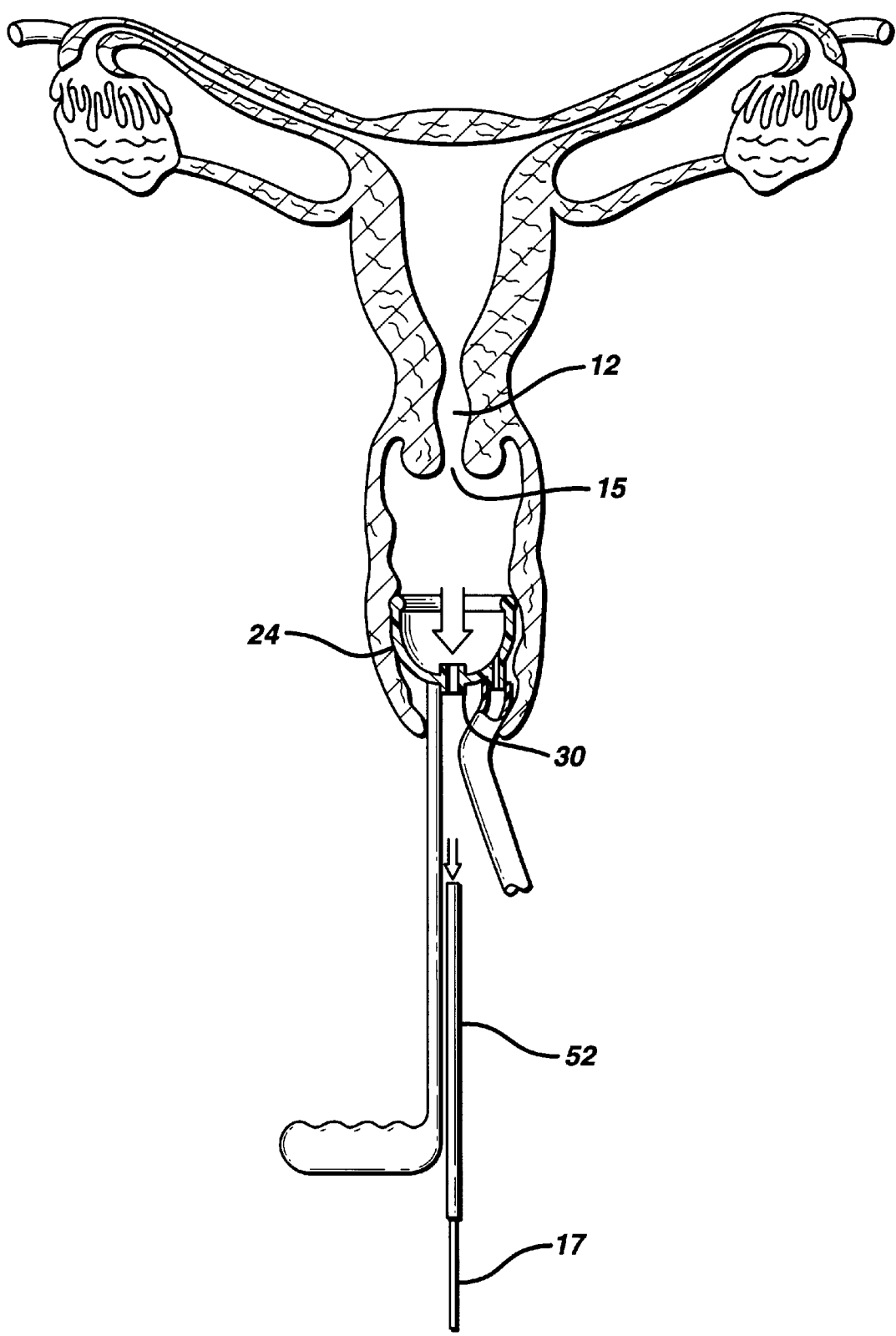

As illustrated in FIGS. 7A–7C, the cervical dam of the invention provides a novel method of performing a procedure wherein fluid is draining from a uterus. The cervical dam 10 may be inserted through the vagina 44 and the base 26 of the cervical dam placed around the cervix 11 so that it snugly surrounds the cervix. The body 24 is positioned so that the aperture 30 is located directly opposite the cervical canal 12.

A medical instrument, such as a surgical sheath 52 containing a hysteroscopic telescope 17, is slidably inserted through the aperture 30, then through the external os 15 into the cervical canal 12. The medical instrument may then be advanced through the cervical canal 12, and hence toward or into the uterus 14. The configuration of the aperture, or a valve contained in the aperture, maintains a relatively liquid-tight seal between the instrument and the cervical dam as the medical instrument is advanced or withdrawn as desired by the physician while the cervical dam is in place.

The uterus may be dilated by the introduction of a distension medium through the cervical sheath during the procedure. This dilation will generally expand the uterine cavity so that the walls of the uterus are sufficiently separated to permit viewing by use of a hysteroscope.

As the procedure continues, additional liquid may be introduced into the uterus, for example, to flush the site immediately in front of the hysteroscope for enhanced viewing, or to maintain a proper liquid environment for procedures such as liquid environment electrosurgery, or to replace distension media that has leaked out of the uterus or been absorbed by the patient.

After the placement of the cervical dam the cervical canal, any fluid draining out of the uterus through the cervical canal will be captured behind the cervical dam. It may be evacuated through the drainage port 36 by gravity or by application of a gentle vacuum on the drainage tube 40. Any fluid draining in this manner may be measured to help determine fluid absorption by the patient during the procedure, and it may be collected for subsequent examination or evaluation.

At the outset of the procedure, as shown for example in FIG. 7A, the handle 42 may be used to insert the cervical dam through the vagina and seat the base of the body of the cervical dam around the cervix. During the procedure, as illustrated in FIG. 7B with the cervical dam in place, the gynecologist may adjust or manipulate the cervical dam using the handle without having to grasp the cervical dam directly. Additionally, the handle may be removed during part or all of the procedure (not illustrated) and reattached when the gynecologist wishes to manipulate or remove the cervical dam. At the end of the procedure, as illustrated in FIG. 7C, the doctor or nurse may remove the cervical dam by pulling on the handle, again without the necessity of actually grasping the device by hand while it is inside the patient's body.

At the conclusion of the procedure when the physician wishes to withdraw the medical instrument, while the cervical dam is in place over the cervical canal, the medical instrument may be withdrawn and the aperture, or valve disposed within the aperture, will close and form a relatively liquid-tight seal. The distension medium draining from the uterus may be evacuated through the drainage tube. When substantially all of the fluid draining from the uterus has been removed, the cervical dam may be removed from the patient. Excessive and unwanted spillage may thus be avoided. Additionally, the amount of liquid removed during and after the procedure may be measured, and by comparing that amount with the amount introduced during the procedure, the amount absorbed by the patient can be calculated.

It is not intended by this description that the use of the cervical dam be limited to hysteroscopic procedures. Other procedures are contemplated whereby control of fluid discharge, fluid monitoring, or protection of the vaginal and skin tissues from fluid draining from the uterus is desired. While several particular forms of the invention have been illustrated and described, it will also be apparent that various modifications can be made without departing from the spirit and scope of the invention.

What is claimed is:

1. A cervical dam for placement over the cervix of a human uterus comprising:
    a body having an interior and an exterior surface, wherein said body is formed of a flexible material;
    said body further having a generally circular base, said body interior surface being spaced apart from the cervix when said base is in place around the cervix of a human uterus to form a cavity;
    said body forming an aperture therein located centrally in said body, said aperture configured to permit passage therethrough of an instrument and to form a generally fluid-tight seal between the aperture and the instrument, wherein said body is formed of an elastomeric membrane, wherein said body is dome shaped, said body having a generally convex exterior surface and a generally concave interior, said body further having an apex opposite said base, said aperture positioned proximate said apex, wherein said body forms a drainage port therein, said drainage port located on said body between said aperture and said base, said drainage port in fluid communication with said interior;
    a valve disposed within said aperture, said valve operable between a closed condition and an open condition, said valve being generally fluid-tight in said closed condition, said valve permitting slidable passage therethrough of a medical instrument when the valve is in said open position, said valve further forming a generally fluid-tight seal with said medical instrument when said medical instrument is contained within said valve, wherein said valve comprises a tubular extension, said tubular extension extending inward from said interior surface;
    a drainage tube in fluid communication with said drainage port;
    an inflatable cuff attached to said body.

2. A cervical dam as in claim 1, wherein said valve is a duck bill valve.

3. A cervical dam as in claim 1, wherein said valve is a universal seal.

4. A cervical dam as in claim 1, wherein the flexible material is latex.

5. A cervical dam as in claim 1 wherein said base is elastomeric.

6. A cervical dam as in claim 1, wherein said inflatable cuff has a roughened exterior surface.

7. A cervical dam as in claim 1 further comprising a handle attached to said body.

8. A cervical dam as in claim 7 wherein said handle is removably attached to said body.

9. A method for performing a procedure comprising the steps of:
    placing a cervical dam over a cervical canal;
    inserting a medical instrument through said dam;
    introducing an amount of fluid into a human uterus;
    draining an amount of said fluid while said cervical dam is in place over the cervical canal;
    determining the amount of fluid introduced into the uterus as a first amount of fluid;
    determining the amount of fluid drained as a second amount of fluid;
    comparing said first amount of fluid with said second amount of fluid; and,
    performing a medical procedure.

* * * * *